United States Patent [19]

Bordoni et al.

[11] Patent Number: 4,703,753
[45] Date of Patent: Nov. 3, 1987

[54] RADIOACTIVE AEROSOL INHALATION APPARATUS

[75] Inventors: Maurice E. Bordoni, Westtown; Ephraim Lieberman, Suffern, both of N.Y.

[73] Assignee: Cadema Medical Products, Inc., Middletown, N.Y.

[21] Appl. No.: 928,826

[22] Filed: Nov. 10, 1986

Related U.S. Application Data

[60] Division of Ser. No. 779,426, Sep. 24, 1985, abandoned, and a continuation-in-part of Ser. No. 707,387, Mar. 1, 1985, Pat. No. 4,598,704, which is a division of Ser. No. 642,718, Aug. 22, 1984, Pat. No. 4,510,929, which is a continuation of Ser. No. 360,370, Apr. 30, 1982, abandoned.

[51] Int. Cl.$^4$ .............................................. A61B 5/08
[52] U.S. Cl. ................................ 128/200.14; 128/1.1
[58] Field of Search ... 128/1.1, 200.18, 200.14–200.16, 128/200.21, 654

[56] References Cited

U.S. PATENT DOCUMENTS

| | | | |
|---|---|---|---|
| 1,839,193 | 1/1932 | Blanchard | 128/200.18 X |
| 3,695,254 | 10/1970 | Blum | 128/1.1 X |
| 3,881,463 | 5/1975 | LeMon | 128/654 |
| 3,915,386 | 10/1975 | Vora | 128/200.18X |
| 4,116,387 | 9/1978 | Kremer et al. | 128/200.18 X |
| 4,251,033 | 2/1981 | Rich et al. | 128/200.21 X |
| 4,333,450 | 6/1982 | Lester | 128/200.14 |
| 4,402,315 | 9/1983 | Tsuda et al. | 128/200.18 |

Primary Examiner—Edward M. Coven
Attorney, Agent, or Firm—Leonard Bloom

[57] ABSTRACT

A radioactive aerosol inhalation apparatus includes a lead-shielded container, having a lid or cover, and a disposable aerosol inhalation device for use in producing properly sized radioactive tagged particles. The disposable device includes a mouthpiece or air passageway communicating means attached to a wye connector for inhalation of the radioactive aerosol and exhalation to an entrapping filter. First and second conduits are respectively provided by flexible tubing from a nebulizer and to the filter. The first and second conduits are interconnected by a third conduit. A one-way valve is provided in the second conduit to allow a subject to exhale therethrough, while preventing inhalation therethrough. A further one-way valve is provided in the third conduit to allow fluid communication from the second conduit to the first conduit, while preventing fluid communication from the first conduit and the nebulizer to the second conduit. The optimum range of particle sizes is generated by producing an aerosol in the nebulizer which has an internal baffle. For ease of handling and to minimize radiation exposures, an entry is provided to add radioactive solution directly into the baffled nebulizer. A method involves using the apparatus to suply an aerosol containing radioactive tagged particles to a subject or patient for treatment and/or diagnosis.

47 Claims, 12 Drawing Figures

RADIOACTIVE AEROSOL INHALATION APPARATUS

CROSS REFERENCE TO RELATED APPLICATIONS

This application is a division of application Ser. No. 779,426, filed 09/24/1985, abandoned, and a continuation-in-part of application Ser. No. 707,387 filed Mar. 1, 1985 and entitled, "AEROSOL INHALATION DEVICE AND METHOD" now U.S. Pat. No. 4,598,704 which is a division of application Ser. No. 642,718 filed on Aug. 22, 1984 and entitled, "DISPOSABLE RADIOACTIVE AEROSOL INHALATION APPARATUS" now U.S. Pat. No. 4,510,929 which is a file wrapper continuation of application Ser. No. 360,370 filed on Apr. 30, 1982 and entitled, "DISPOSABLE AEROSOL INHALATION APPARATUS," now abandoned.

BACKGROUND OF THE INVENTION

This invention relates to a radioactive aerosol inhalation apparatus which includes a disposable pulmonary inhalation device which is comprised of a means to generate properly sized aerosol particles, more particularly such particles containing radioactive material, for subsequent inhalation. For various types of diagnostic testing and treating, it is necessary to have patients inhale radioactive materials in order, for example, to perform ventilation studies of the lung. In addition, it is well known that the hospital staff who handle radioactive materials need protection against the problems associated with ionizing radiation exposure; this apparatus provides for adequate shielding to meet this requirement. For flexibility, the apparatus is portable, the device is disposable, and the apparatus is inexpensive. The apparatus provides the capability to easily and safely add radioactive solution to the nebulizer, for aerosolizing the radioactive solution to the proper aerosol particle size, and to collect the radioactive aerosol particles in a properly shielded filter. The device is also suitable for delivering nonradioactive aerosols to a subject undergoing treatment or study. The device and apparatus can be used in conjunction with a respirator.

This technique of administering a radioactive aerosol is an improvement over existing modalities in that the radiation dose to the patient is less, the probability of radioactive contamination within the hospital room, as compared to other methods is diminished, and the flexibility to obtain images of various anatomical positions of the patient is increased.

Relevant prior art United States Letters Patents are:

| U.S. Pat. No. | Inventor(s) | Date Issued |
|---|---|---|
| 3,097,645 | Lester | Jul. 16, 1963 |
| 3,172,406 | Bird et al. | Mar. 9, 1965 |
| 3,243,100 | Adams | Mar. 29, 1966 |
| 3,666,955 | Suprenant et al. | May 30, 1972 |
| 3,695,254 | Blum | Oct. 3, 1973 |
| 3,762,409 | Lester | Oct. 2, 1973 |
| 3,769,967 | Jones el al. | Nov. 6, 1973 |
| 3,777,742 | Aumiller et al. | Dec. 11, 1973 |
| 3,881,463 | Le Mon | May 6, 1975 |
| 3,976,050 | Glasser et al. | Aug. 24, 1978 |
| 4,116,387 | Kremer, Jr. et al. | Sep. 26, 1978. |

SUMMARY OF THE INVENTION

The present invention relates to a new and improved aerosol inhalation and apparatus which generates properly sized radioactive particles for performing ventilation studies of the lungs. A radioactive solution is added to a baffled nebulizer and the solution aerosolized using air or oxygen. The aerosolized radioactive particles are then breathed into the lungs and data for assessing lung function may be recorded by means of a radiation particle counting device such as a scintillation camera and associated software. The radioactive aerosol is administered to the patient through a mouth-piece or face mask or a tubular trachea-communicating member, via a conduit of valved flexible tubing.

It is, therefore, a principal object of the present invention to provide an apparatus which includes a disposable radioactive aerosol inhalation device capable of allowing pulmonary ventilation tests that deliver proper-sized particles to lung areas, controlled delivery and recovery of radioactive aerosolized particles and shielding to minimize exposure of personnel to problems associated with ionizing radiation.

Another object of the invention is to provide an apparatus which incorporates a conduit and valve arrangement which is activated during the breathing cycle of the patient or subject to assist in permitting the individual to inhale and exhale with the minimum of effort during the generation of radioactive aerosol from within the system.

An additional object of the invention is to provide an apparatus which incorporates a conduit arrangement and two valves which allows an individual to breathe with minimum effort during generation of radioactive aerosol from within the apparatus.

A further object is to provide a radiation-shielding container which includes therein a mechanism which may be manipulated by a user to aid in removing a disposable device therefrom, while keeping the radiation exposure to a minimum.

A still additional object of the invention to provide an aerosol inhalation apparatus for supplying mist to a subject which is simple, inexpensive and requires a single valve which can be positioned within a radiation-shielding container.

A still further object of the invention is to provide an apparatus of the character described which will minimize the radiation exposure to the patient or subject and the technician administering the diagnostic test or treatment. Adequate shielding in the form of lead surrounds the baffled nebulizer and the entrapping filter, reducing the problems associated with exposures to ionizing radiation.

Another object of the invention is to provide an apparatus of the character described in which images or pictures from various anatomical positions can be taken further increasing the usefulness of this diagnostic method of evaluating disease of the bronchus, the bronchioles, and the alveolar sites of the lung.

A further object of the invention is to provide an apparatus of the character described which will reduce the radioactive contamination of the facilities, the equipment, and most importantly, the attending medical personnel.

In one aspect the present invention can be seen as being an aerosol inhalation apparatus for supplying an aerosol mist containing radioactive tagged particles to a subject. The apparatus includes a reusable radiation-shielded container having lid means, whereby the contents of the container are readily accessible. The apparatus also includes a disposable radioactive aerosol inhalation device, the device including first and second conduit means in the container and passing therethrough. Means for communicating with an air passageway of a subject are connected to the first and second conduit means externally of the container. Valve means are provided for controlling exhalation from the second conduit means. A nebulizer is positioned within the container and connected to the first conduit means. Means positioned at least in part within the container and in fluid communication with the nebulizer are provided for allowing introduction of radioactive solution from outside the container into the nebulizer. Means associated with the nebulizer are provided for effectively generating an aerosolized mist carrying airborne radioactive tagged particles. Means are provided for introducing a mixture of air or oxygen and the mist into the first conduit means. Third conduit means is provided within the container interconnecting the first conduit means and the second conduit means. Entrapping filter means is provided in the container and connected to the second conduit means for removing the aerosol exhaled. The container may be reused and the device may be discarded after each use.

The invention can also be viewed as an aerosol inhalation apparatus for supplying an aerosol mist containing radioactive tagged particles to a subject. The apparatus includes a reusable generally cylindrical walled container having a closed bottom and an open top. Radiation-shielding means is provided within the wall and bottom of the container. The container has first, second and third openings, perferably realized as slots, formed therein, the openings being at the top portion of the container and being circumferentially spaced from each other. A radiation-shielding lid means covers the container top portion. A disposable pulmonary inhalation device includes nebulizing means in the container and entrapping filter means within the container. Means received in the first of the openings and includes a conduit connected to the nebulizer means for introducing a radioactive liquid into the nebulizer means. Means are associated with the nebulizer means for generating an aerosolized mist having a plurality of radioactive tagged particles. Inhalation conduit means is received in the second of the openings and connected to the nebulizer means. Exhalation conduit means is received in the third of the openings and is connected to the filter means. Further conduit means within the container interconnect the inhalation conduit means and the exhalation conduit means. The container may be reused and the device may be discarded after each use.

The invention, somewhat more specifically, can be seen as an aerosol inhalation apparatus for supplying an aerosol mist containing radioactive tagged particles and air and/or oxygen to a subject. The apparatus includes a reusable radiation-shielding container having lid means, whereby the contents of the container are readily accessible. The apparatus also includes a disposable radioactive aerosol inhalation device, the device including first and second conduit means in the container and passing therethrough. Means for communicating with an air passageway of a subject are connected to the first and second conduit means externally of the container. Valve means are provided for controlling exhalation from the second conduit means. A nebulizer is positioned within the container and connected to the first conduit means. Means positioned at least in part within the container and in fluid communication with the nebulizer are provided for allowing introduction of radioactive solution from outside the container into the nebulizer. Means in fluid communication with a source of air and/or oxygen and with said nebulizer are provided for generating an aerosolized mist carrying airborne radioactive tagged particles. Means are included for introducing a mixture of air and/or oxygen, and the mist into the first conduit means, third conduit means within the container interconnecting the first conduit means and the second conduit means. Entrapping filter means is provided in the container and connected to the second conduit means for removing the aerosol exhaled. The container may be reused and the device may be discarded after each use.

The means carried by the container for allowing introduction of a radioactive solution into the nebulizer in a realized embodiment includes means in fluid communication with the nebulizer and with the first conduit means for permitting entry of ambient gas or atmospheric air or gas from a respirator into the nebulizer and into the first conduit means.

The means for allowing introduction of a radioactive solution is preferably an angulated portion allowing a needle to extend into the container at an angle with respect to vertical to minimize exposure to radiation.

The apparatus has a settling baffle in the nebulizer to generate properly sized aerosol particles of less than substantially one micron.

The nebulizer desirably includes a diffuser and gas orifice, the settling baffle being positioned above the diffuser and the gas orifice for permitting aerosol particles larger than substantially one micron to remain in the nebulizer.

From a different viewpoint, the invention can be seen as an aerosol inhalation apparatus for supplying an aerosol mist containing radioactive charged particles to a subject. The apparatus includes a reusable generally cylindrical walled container having a closed bottom and an open top. Radiation-shielding means are provided within the wall and bottom of the container. The container has first, second and third openings formed therein, respectively, these openings are at the top portion of the container and are circumferentially spaced from each other. Radiation-shielding lid means covers the container portion top. A disposable pulmonary inhalation device, including nebulizing means, are positioned within the container. Entrapping filter means is provided within the container. Means received in the first of the openings includes a conduit connected to the nebulizer means for introducing a radioactive liquid into the nebulizer means. Means associated with the nebulizer means are provided for generating an aerosolized mist having a plurality of radioactive tagged particles. Inhalation conduit means is received in the second of the openings and is connected to the nebulizer means. Exhalation conduit means is received in the third of the openings and is connected to the filter means. Further conduit means interconnect the inhalation conduit means and the exhalation conduit means. The container may be reused and the device may be discarded after each use.

Somewhat more specifically, the invention can be viewed as an aerosol inhalation apparatus for supplying an aerosol mist containing radioactive charged particles and air and/or oxygen to a subject. The apparatus includes a reusable generally cylindrical walled container having a closed bottom and an open top. Radiation-shielding means are provided within the wall and bottom of the container. The container has first, second and third openings formed therein, respectively, these openings being at the top portion of the container and being circumferentially spaced from each other. Radiation-shielding lid means are provided on the top portion of the container. A disposable pulmonary inhalation device which includes nebulizing means is positioned within the container. Entrapping filter means is provided within the container. Means received in the first of the openings includes a conduit connected to the nebulizer means for introducing a radioactive liquid into the nebulizer means. Means associated with the nebulizer means are provided for generating an aerosolized mist having a plurality of radioactive tagged particles. Inhalation conduit means is received in the second of the openings and is connected to a source of air and/or oxygen and to the nebulizer means for receiving a mixture of air and/or oxygen and the mist. Exhalation conduit means is received in the third of the openings and is connected to the filter means. Further conduit means interconnect the inhalation conduit means and the exhalation conduit means. The container may be reused and the device may be discarded after each use.

The first, second and third openings are realized as respective slots extending downwardly from the top edge of the container.

In its apparatus aspect, the invention can be seen as an aerosol inhalation device for supplying an aerosol mist to a subject. The device includes a first and second conduit means. Means for communicating with an air passageway of a subject is connected to the first and second conduit means. Valve means is provided for controlling exhalation from the second conduit means. A nebulizer coupled to said first conduit means is provided. Means in fluid communication with the nebulizer allows introduction of liquid into the nebulizer. Means associated with said nebulizer generate an aerosolized mist carrying airborne particles. Means are present for introducing a mixture of air and/or oxygen and the mist into the first conduit means.

In its method aspect the disclosure can be viewed as including a method for the diagnosis or treatment of pulmonary diseases. The method includes providing a nebulizer means, introducing a radioactive solution into the nebulizer means, and generating in the nebulizer means an aerosolized mist containing radioactive tagged particles of less than a given size, preferably less than substantially two microns, and still more preferably less than substantially one micron.

The method desirably includes delivering the aerosolized mist containing radioactive tagged particles to a subject, and filtering exhalant from the subject to capture exhaled radioactive tagged particles.

From one vantage point the disclosure can be viewed as including a method useful in the diagnosis or treatment of pulmonary diseases. The method includes providing a nebulizer, an entrapping filter and conduit means, which are connected to allow a subject to inhale and to exhale via the conduit means. The method involves providing a reusable radiation-shielding container, positioning the nebulizer, the entrapping filter and at least portions of the conduit means within the radiation-shielding container. Thereafter the method provides introducing a radioactive solution into the nebulizer, generating in the nebulizer an aerosolized mist containing radioactive aerosol particles of less than substantially a given size, preferably less than substantially two microns and still more preferably less than substantially one micron, allowing a subject to inhale and to exhale the aerosolized mist via the conduit means, and entrapping exhaled radioactive particles in the filter.

The method desirably includes the steps of removing the nebulizer, the entrapping filter and the conduit means from the lead-shielded container and disposing of the nebulizer, the entrapping filter and the conduit means.

The method desirably includes the step of permitting aerosol particles of larger than substantially two microns (preferably one micron) to remain in the nebulizer, while allowing smaller aerosol particles to enter the conduit means.

The invention in one aspect can be seen as an aerosol inhalation apparatus for supplying an aerosol mist containing radioactive tagged particles to a subject and which includes a disposable aerosol inhalation device and a radiation-shielding container. At least a portion of the device is removably fixed within the container. A mechanism at least partially positioned within the container and accessible from outside the container is provided for unfixing the device from said container.

From another vantage point the invention can be viewed as an aerosol inhalation device for supplying an aerosol mist to a subject, the device including a first and a second conduit. Means for communicating with an air passageway of a subject are connected to the first and second conduits. Valve means is provided for controlling exhalation from the second conduit. A throttle is coupled to the first conduit. A nebulizer is coupled to the first conduit via the throttle. Means in fluid communication with the nebulizer allows introduction of liquid into the nebulizer. Means associated with the nebulizer are provided for generating an aerosolized mist carrying airborne particles. A third conduit interconnects the first conduit and the second conduit. Means are provided for introducing a mixture of air and/or oxygen, and the mist into the first conduit.

The invention can be seen as an aerosol inhalation device for supplying an aerosol mist to a subject, the device including a first and a second conduit. Means for communicating with an air passageway of a subject are connected to the first and second conduits. Valve means are provided for controlling exhalation from the second conduit. A throttle is coupled to the first conduit. A nebulizer is coupled to the first conduit via the throttle. Means in fluid communication with the nebulizer is provided for allowing introduction of liquid into the nebulizer. Means associated with the nebulizer generates an aerosolized mist. Means are provided for introducing a mixture of air and/or oxygen, and the mist into the first conduit.

Other features and advantages of the invention in its apparatus and method aspects, will become more readily apparent from the following detailed description, when taken in conjunction with the accompanying drawings.

BRIEF DESCRIPTION OF THE DRAWINGS

FIGS. 10 and 11 are respective pictorial views of an inhalation apparatus in accordance with the present invention, FIG. 10 showing the lid and port shield off the container, while FIG. 11 shows the lid and port shield on the container.

DESCRIPTION OF THE PREFERRED EMBODIMENTS

Figure 1:
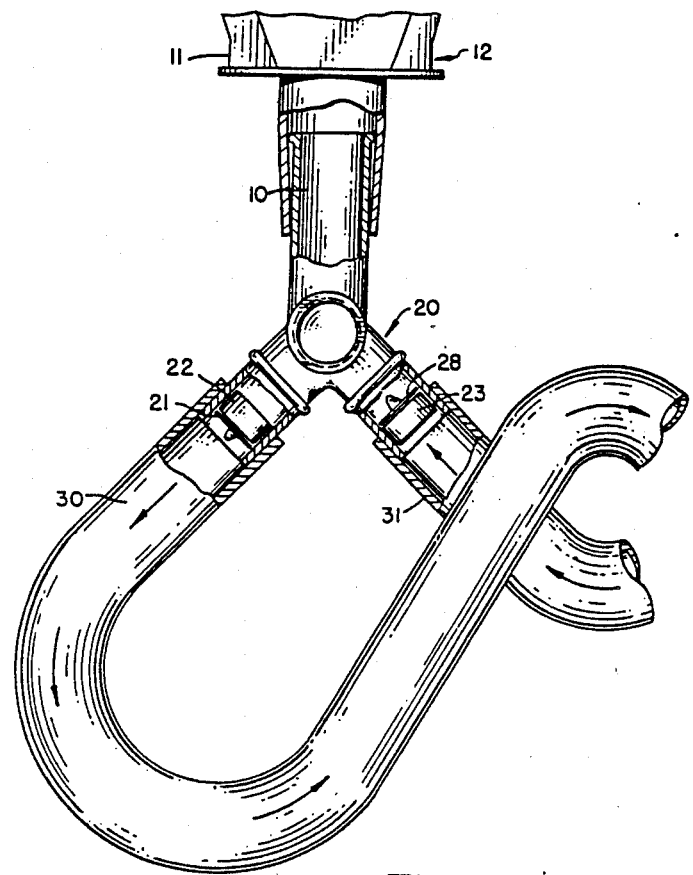
FIG. 1 is an elevational diagramatic perspective view of a portion of the aerosol inhalation apparatus as disclosed in the above-mentioned patent application Ser. No. 707,387 of which the instant application is a continuation-in-part.

Referring to FIG. 1, there is shown a disposable aerosol inhalation device for use in producing radioactive tagged particles in accordance with an embodiment of the invention disclosed in patent application Ser. No. 707,387. A patient or subject (not shown) breathes through a mouthpiece 12 having flanges 11 to permit a tight fit in the mouth. The mouthpiece 12 is attached to a tubular extension 10 of a wye 20 containing two one-way valves, inlet valve 22 to the device and exit valve 23 from the device. The valves 22 and 23 are positioned to effect the proper movement of radioactive particles through provided conduits 30 and 31. As shown in FIG. 1, when the patient inhales, the diaphragm 28 of the valve 23 opens and permits the radioactive particles to enter the mouthpiece 12 and ultimately to deposit in the lungs. During inhalation, diaphragm 21 of the valve 22 remains closed due to the pressure differential across the valve 22. At exhalation, the valve 23 closes and the valve 22 opens to permit the exhalant to pass the valve 22, travel through the conduit 30, and into an entrapping filter 40 (FIG. 4).

Figure 4:
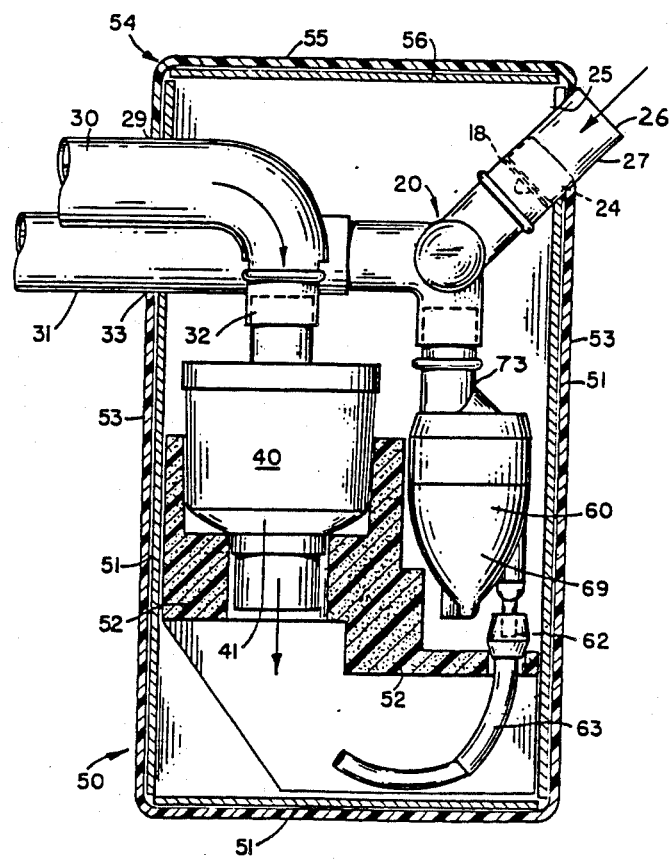
FIG. 4 is a fragmentary perspective diagramatic view of an apparatus which includes a portion of the apparatus of FIG. 1 illustrating the shielded container for the nebulizer and the entrapping filter, as disclosed in patent application Ser. No. 707,387.

FIG. 4 can be seen as illustrating the operational technique as follows: The radio pharmaceutical liquid to be aerosolized is added to the system through the diaphragm 18 of the valve 24 contained in wye leg 27. The wye leg 27 protrudes through lead-shielded container 50 at portal 25, a downwardly extending slot (opening) being provided on the sidewall of the container 50 for this purpose. The entrance portal 26 to the wye leg 27 is set at an angle to minimize direct radiation streaming from the solution of radioactive liquid contained in baffled nebulizer 60 within the container 50 when the apparatus is in operation. The injected radioactive solution deposits in the baffled nebulizer 60 at approximate level 69. Oxygen or air from a tank (not shown) is directed into the system at approximately 10 liters per minute via a flexible tube 63 which is connected from the tank to the bottom of the nebulizer 60 via tubular stem 62. The oxygen or air mixes with the radioactive solution to form airborne particles. The airborne particles then pass through the conduit 31, through the valve 23, and into the lungs or a subject or patient. The exhaled air including aerosol passes through the valve 22 to the conduit 30, and into a filter 40 via a tubular extension 32, and the aerosol becomes entrapped in the filter 40. The patient breathes the aerosolized radioactive particles until enough radiation from the of the subject or patient lungs is externally detected by sensing with radioactive detectors. The filter 40 may be a conventional disposable conductive anesthesia bacteria filter; one example of such a filter sold under stock number 225-2615-700 by Ohio Medical Products, a well known American company.

Figures 2, 3:
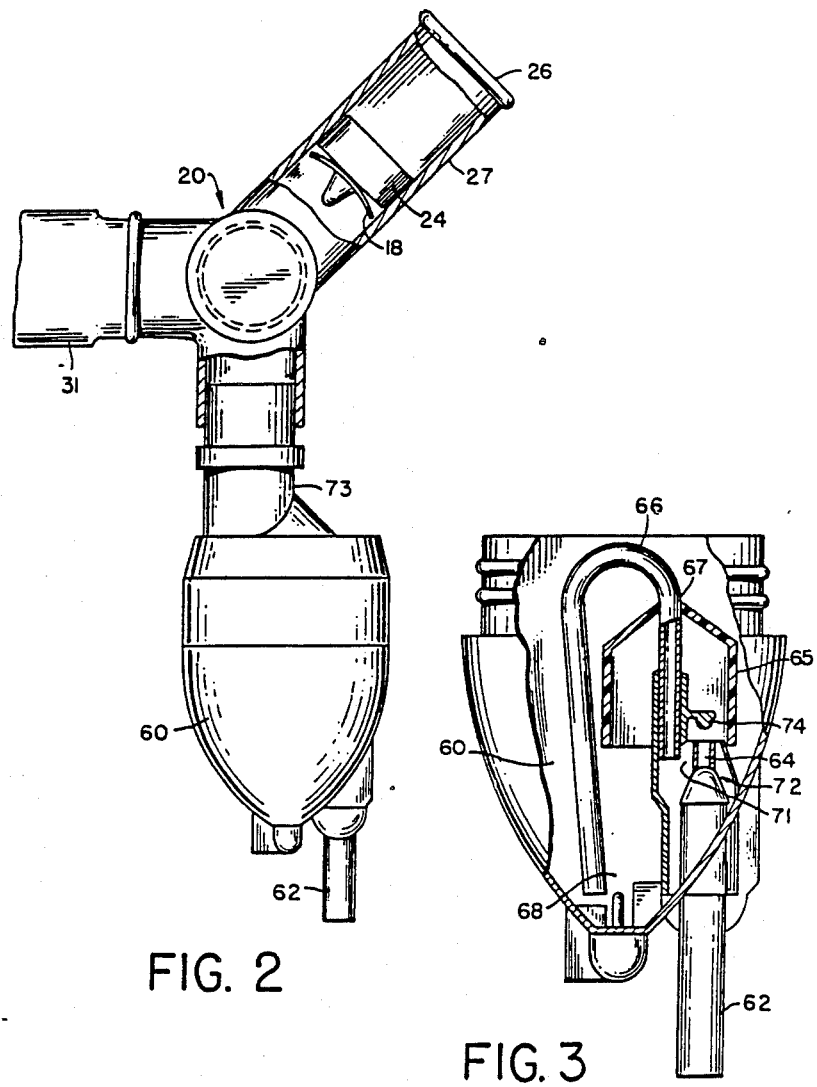
FIG. 2 is a fragmentary perspective diagramatic view of a portion of the apparatus of FIG. 1 illustrating the angulated wye and valve through which radioactive solution is added to the baffled nebulizer, as disclosed in patent application Ser. No. 707,387.
FIG. 3 is a fragmentary perspective diagramatic view of a portion of the apparatus of FIG. 1 illustrating the modified nebulizer with its internal baffle, as disclosed in patent application Ser. No. 707,387.

FIG. 2 illustrates entry port the 26 for the radioactive solution that enters the baffled nebulizer 60, as disclosed in patent application Ser. No. 707,387. The radioactive solution to be aerosolized is carried to entry port 26 in a shielded syringe to minimize radiation exposures to the administering technician and subject or patient (not shown). The entry port 26 and wye leg 27, shown in FIG. 4 protrude from side of the lead-shielded container 50 (FIG. 4) at an approximate angle of forty-five degrees. The angulation of the entry port 26 reduces the amount of radiation exposure to the administering technician due to streaming, once the radioactive solution has entered the nebulizer system. The solution enters the system through the diaphragm 18 of the valve 24. The needle of the syringe containing radioactive solution (not shown) pushes the diaphragm 18 aside and while the orifice of the needle (not shown) protrudes past the diaphragm, the radioactive solution is injected into the nebulizer system. Check valve 24 is approximately 22 millimeters in diameter. To ease breathing of the subject or patient, the valve 24 also acts as an inlet valve in that each time the subject or patient inhales, he receives a portion of air from the atmosphere or other ambient; for example, an oxygen ambient provided within an oxygen tent or the like. In addition, the valve 24 acts as monitor to the breathing function of the subject or patient. The administering technician observes movement of the valve diaphragm 18 each time the subject or patient inhales to insure he is breathing normally.

FIG. 3 illustrates the nebulizer 60 fitted with an elongated conical baffle that permits proper sized radioactive particles to enter the lungs of a subject or patient, as disclosed in application Ser. No. 707,387. Oxygen enters the nebulizer 60 through a stem 62. The oxygen gas passes through a nozzle assembly 72 extending into the container 50. The nozzle assembly 72 includes gas nozzle 64 and a coaxial solution nozzle 71 with approximately perpendicular positioned orifices. Extending above the nozzle assembly is an elongated conical settling baffle 65 formed of plastic and having a volume of approximately three cubic centimeters. The settling baffle 65 reduces hyperdeposition of large particles typically greater than two microns from entering the lungs of the subject or patient. The aerosolized radioactive particles enter the baffle area at the diffuser orifice of the gas nozzle 64 and through sedimentation, impaction and turbulence within the baffle 65, particles greater than two microns settle to the interior bottom portion 68 of the nebulizer 60 and particles typically less than two microns enter conduit 73 (FIGS. 2, 4) above the nebulizer and are inhaled by the subject or patient (not shown).

The top of the conical baffle 65 has a symmetrical opening 67 of approximately three millimeters in diameter that permits entry of conduit tubing 66 which carries radioactive solution from the nebulizer reservoir to the orifice 71. The radioactive solution exiting the orifice 71 mixes with incoming oxygen and is aerosolized through the orifice-diffuser arrangement which includes a diffuser 74. The particles are properly sized while engaging in turbulent action within the baffle 65.

FIG. 4 illustrates, as in patent application Ser. No. 707,387 the lead-shielded container 50 which houses the entrapping filter 40, the baffled nebulizer 60 and a supporting insert 52. The container 50 has an approximate volume of three liters and consists of outer plastic laminate 53 and lead shielding 51 laminated together and comprising average thicknesses of two to four millimeters. The lead shielding 51 is necessary to minimize radiation exposure to the administering technician and subject or patient during the ventilation treatments or studies of the lung. The plastic or equivalent material insert 52 sets the entrapping filter 40 in a fixed position, using filter portion 41 as a seat. The baffled nebulizer 60 is seated in similar fashion, using reservoir bottom end portions and the stem 62 thereof. Slots or openings 29 and 33 of approximately 25 millimeters in width or diameter are made through the shielded container 50 to allow the conduits 30 and 31 and the oxygen tube 63 to exit the container 50 and to be easily removed therefrom. The additional slot 25 of approximately five millimeters width is made through the container 50 exposing an entry port or injection site for the radioactive solution. The angle of the slot or opening 25 with respect to the horizontal is 90° and is made to minimize radiation streaming from the shielded container 50. A cap or lid 54 constructed of plastic laminate 55 and lead shielding 56 laminated together are of the previously described thickness of the plastic laminate 53 and the lead shielding 51. The cap or lid 54 is removable to permit easy access and exit of the disposable portions of the apparatus at commencement and termination of the treatment or diagnostic procedures.

A particularly advantageous radiation-shielding container with its associated components is illustrated in FIGS. 5, 6, 10 and 11. The container is in the form of a hollow cylinder composed of an upwardly extending vertical wall member 70, the bottom of which is closed by a circular bottom member 71, which is preferrably intregal with the wall member 70. The hollow cylinder wall member 70 is opened at the top thereof. A lid 72, which has a downward extending continuous lip 73 of arcuate shape spaced inwardly from its circumferential edge, is provided. The outer diameter of the downwardly extending lip 73 is chosen to conform with the inner diameter of the cylindrical wall member 70 so that the lid 72 may be easily placed and removed from the opened top thereof. The cylindrical wall member 70, the bottom closing member 71 and the lid 72 are made of suitable radiation-shielding material of sufficient thickness to provide protection against radiation from within the container. The cylindrical wall member 70, the bottom closing member 71 and the lid 72 can be of laminated construction, if desired, the construction corresponding to that of the container, bottom and lid illustrated in FIG. 4. An upstanding post 74 having a flange extending from its uppermost extent, is positioned centrally on the lid 72, providing a means to allow a user to grasp the post between fingers and a thumb and place the lid on and remove the lid from the opened top of the cylindrical wall member 70.

Figure 10:
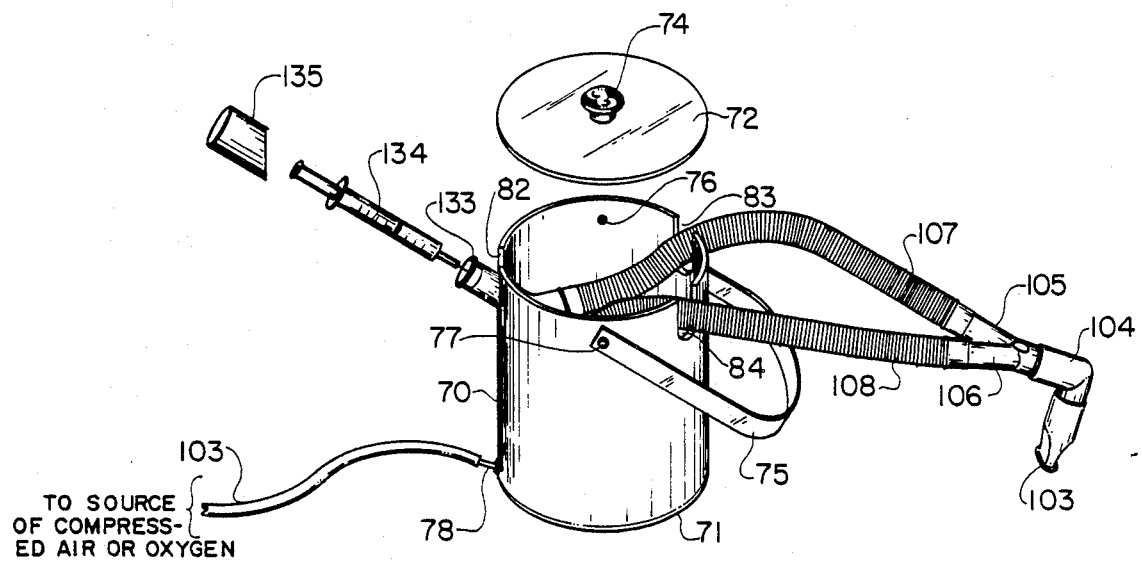
Figure 11:
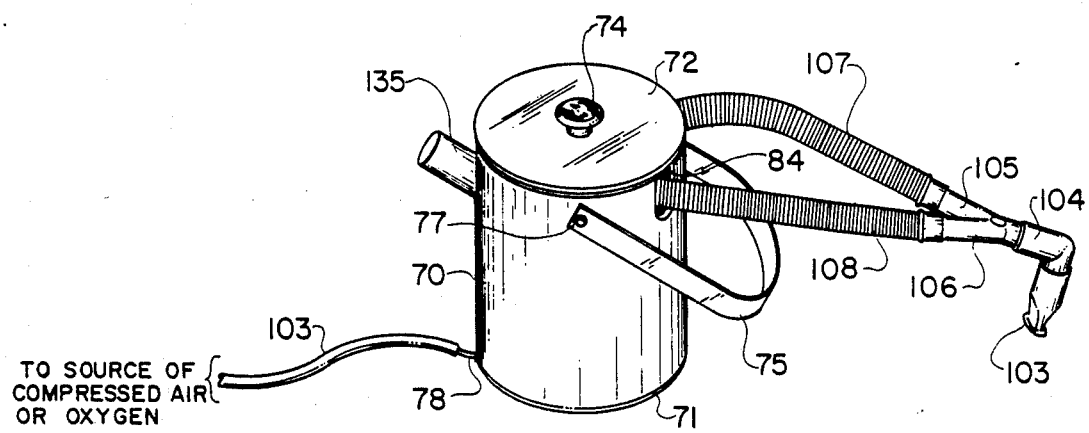

A carrying handle 75, preferrably made of a plastics material, is provided with apertures in the vicinity of its ends, these apertures being aligned with corresponding apertures in the cylindrical wall member 70 and held in place by a pair of suitable rivets 76 and 77 which extend through the aligned apertures. The apertures in the carrying handle 75 do not provide a tight fit against the rivets 76 and 77, allowing the handle 75 to be rotated about an axis defined by the rivets 76 and 77 and the aligned apertures so that the handle 75 can be moved from its upwardly extending carrying position to the left or right (as shown in FIGS. 10 and 11) to allow one to easily remove the lid 72 from the container.

Figure 5:
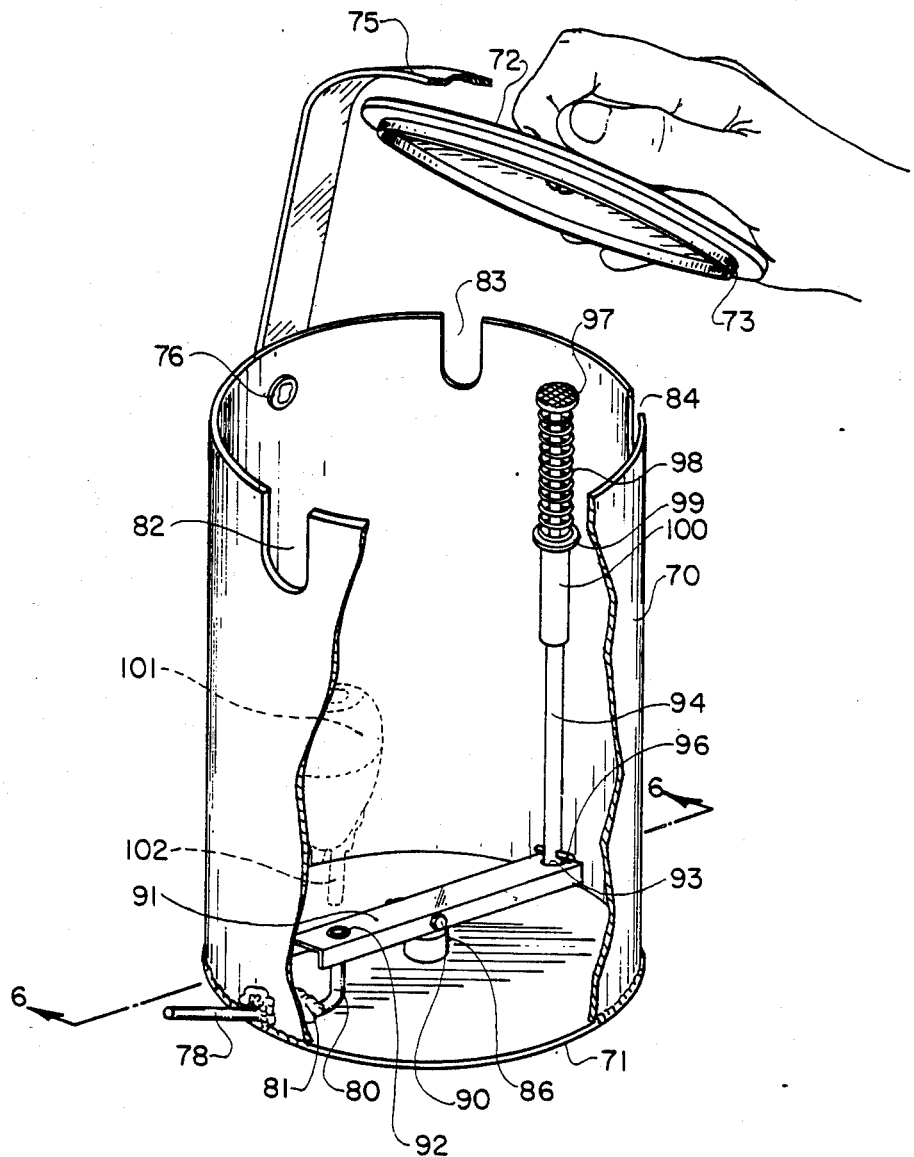
FIG. 5 is a pictorial view of a variant of a radiation-shielding container provided with a lid and which can be used in an inhalation apparatus of the present invention, its cylindrical wall being broken away to allow viewing of its internal construction.
Figure 6:
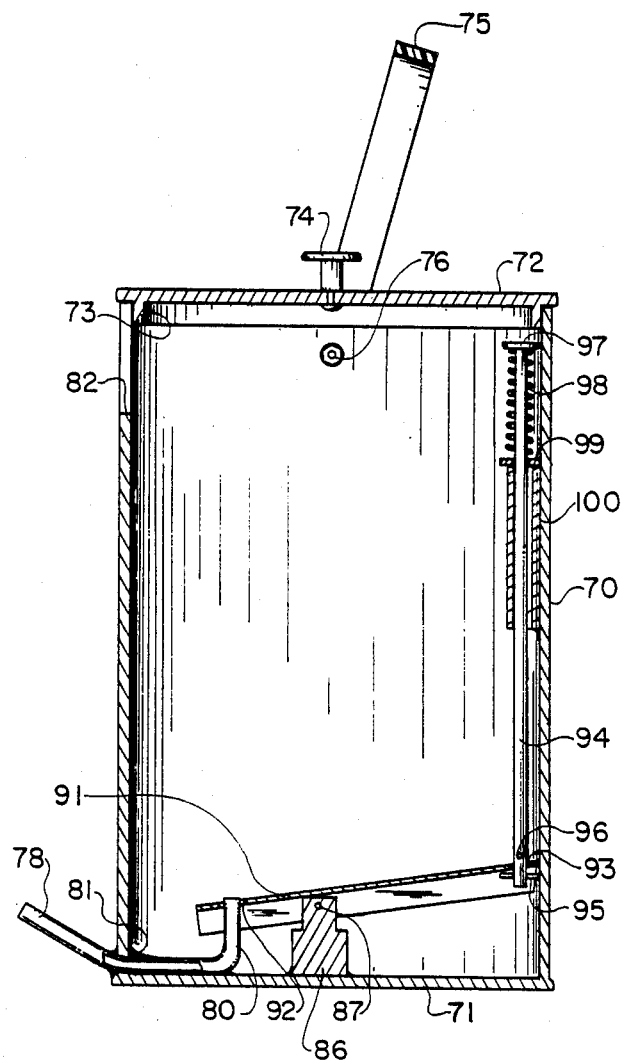
FIG. 6 is a cross-sectional view of the container of FIG. 5, the section having been taken along section line 6—6 in FIG. 5.

A tubular member 78, via which air and/or oxygen is to be supplied from flexible hose 103 (FIGS. 10, 11), extends through the cylindrical wall member 70 in the vicinity of the bottom-closing member 71, the end of the tubular member 78 positioned within the cylindrical member 70 being bent upwardly to define an upwardly extending portion 80, visible in FIGS. 5 and 6. The tubular member 78 can advantageously be welded or soldered to the cylindrical wall member 70 by a weld or solder material 81.

The top edge of the cylindrical, wall member 70 is provided with downwardly extending slots 82, 83 and 84, the slots being equally spaced from one another about the circumference of the top of the wall member 70. The bottoms of each of the downwardly extending slots 82, 83 and 84 is preferrably arcuate to provide respective bearing surfaces for members having circularly arcuate outer surfaces, such as hollow conduits of circular cross section.

An upwardly extending, short cylindrical post 86 is positioned centrally on an inner surface of the bottom-closing member 71, the post being fixed thereto by a conventional means such as a weld. As illustrated the upstanding, cylindrical post 86 has a portion thereof near its free end of somewhat reduced diameter (see FIG. 6). An aperture 87 (FIG. 6 is provided through the portion of the post 86 of reduced diameter. A bolt 90 (FIG. 5) extends through the aperture 87 and through aligned apertures in side walls of an inverted U-shaped member 91 made of metal, the bolt 90 providing a pivot point for the inverted U-shaped member 91. In the vicinity of one end of the inverted U-shaped member 91, an aperture 92 is provided, this aperture being aligned with the open end of the upstanding portion 80 of the tubular member 78. The other end of the inverted U-shaped member 91 is provided with a further aperture 93 through which an end of a vertically extending rod 94 is positioned, the rod 94 being held within the aperture 93 by a pair of pins 95 and 96 which extend through the rod on opposite sides of the upper portion of the inverted U-shaped member 91, as best seen in FIGS. 5 and 6. The other end of the vertically extending rod 94 is provided with a horizontally extending flange 97 which has a knurled upper surface, allowing a user to place his or her finger thereon and depress the rod 94 downwardly against the force of a helical spring 98 which extends between the downwardly facing surface of the knurled flange 97 and a second flange 99 which extends outwardly from a cylindrical tubular member 100 which guides the rod and is fixed to the inner wall of the cylindrical member 70 by conventional means, such as a weld, and through which the vertically movable rod 94 extends. A nebulizer 101, illustrated in phantom FIG. 5 is to be positioned within the radiation-shielding container so that its integral tubular air/oxygen input conduit 102 can be positioned into the open end of the upstanding portion 80 of the tubular member 78, as indicated in FIG. 5. Oxygen and/or air is to be provided through the tubular member 78 and fed into the nebulizer 101, via the tubular conduit 102 and the upstanding portion 80 of the tubular member 78. The flexible hose 103 (FIGS. 9 and 10) is provided to connect the source of oxygen and/or air under pressure to the tubular member 78.

The force of the spring 98 causes the inverted U-shaped member 91 to assume the position illustrated in FIG. 6, allowing one to position the nebulizer 101 so that its conduit 102 is in fluid communication with the upstanding portion 80 of the tubular member 78. During infusion of a subject with aerosol mist from the nebulizer 101, the inverted U-shaped member 91 and the vertically extending rod 94 would remain positioned as illustrated in FIGS. 5 and 6. At the conclusion of studies of a single patient, the examining physician or technician is able to easily remove the lid 72 by momentarily placing one of his or her fingers over the knurled upper surface of the flange 97 and depress the rod 94 against the pressure of the spring 98, causing the inverted U-shaped member 91 to rotate about the axis defined by the bolt 90. This causes the end of the inverted U-shaped member 91 immediately beneath the nebulizer 101 to move upwardly against a surface on the lower portion thereof and effect disconnection of its tubular air or oxygen receiving conduit 102 and thus the complete nebulizer from the upstanding portion 80 of the tube 78. This allows the physician or technician to minimize radiation exposure from within the radiation-shielding container. The nebulizer 101, together with its associate disposable components of the device may be readily removed from the radiation-shielding container and disposed of, without subjecting the physician or technician to inordinate and unnecessary exposure to radiation.

Figure 7:
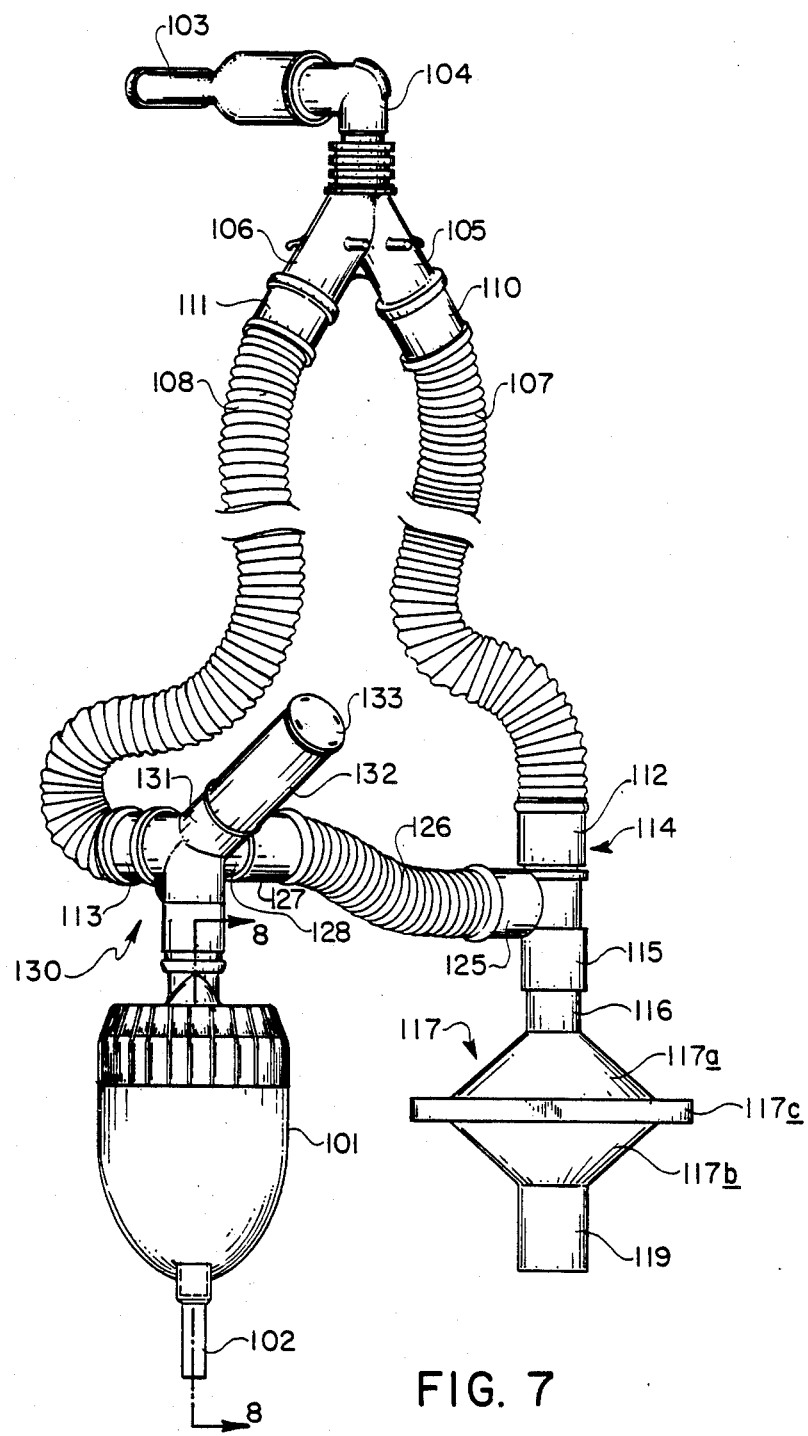
FIG. 7 is a pictorial view of a preferred device which, with the container of FIGS. 5 and 6, constitutes a preferred embodiment of an inhalation apparatus in accordance with the present invention and which, with the container illustrated in FIG. 4, constitutes another embodiment of the invention.
Figure 12:
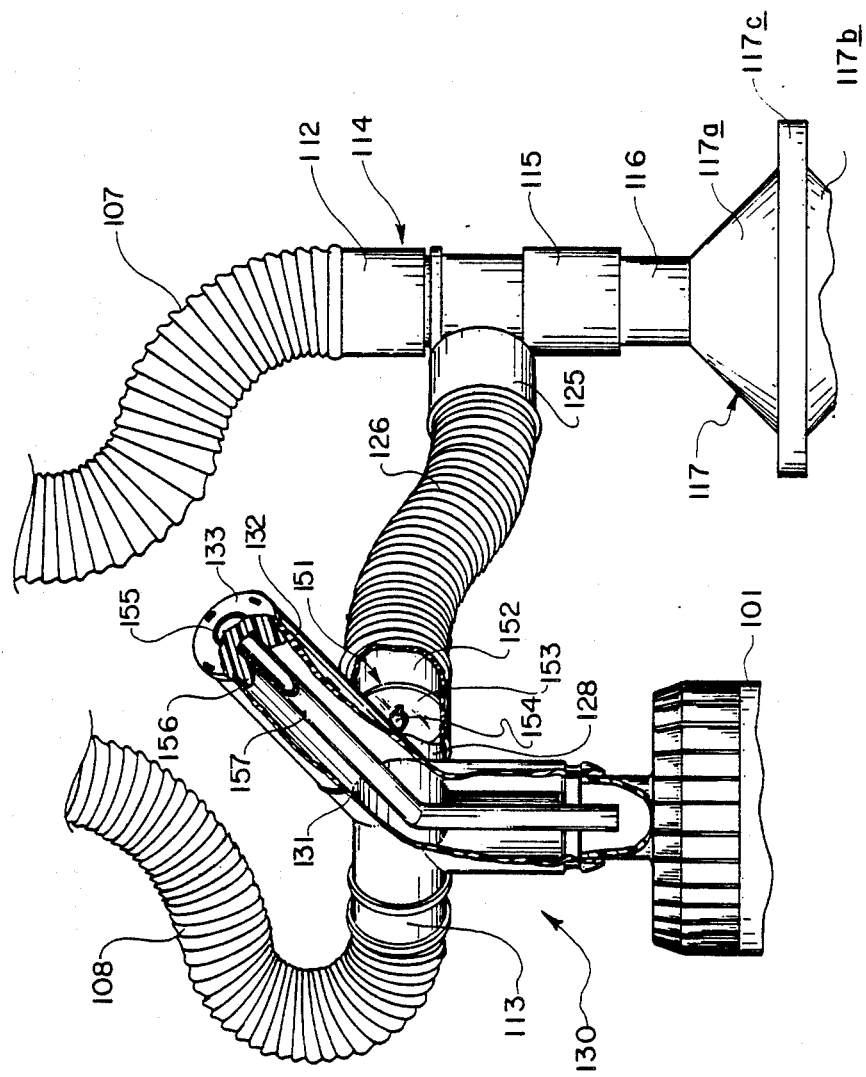
FIG. 12 is a pictorial view, partially broken away of a portion of the device of FIG. 7, the placement of a second one-way valve, and position of a tube associated with the self-sealing closure member being visible.

A preferred aerosol inhalation device for supplying aerosol mist to a subject in a particularly preferred embodiment is to be described generally, with reference to FIGS. 7, 10 and 11. As shown in FIGS. 7, 11 and 12 the disposable device includes a mouthpiece 103 which is designed to communicate with an air passage of a subject, via the subject's mouth cavity and throat. It is to be appreciated that the mouthpiece could be replaced by a tubular member suitable for being inserted into the trachea of a subject, the tubular member being provided with an associated carrying flap or the like which could be sutured to the neck of a subject. The mouthpiece 103 is arranged to telescope over an end of a tubular elbow 104, its free end being connected to and being in fluid communication with a pair of rigid tubular members 105 and 106 providing a Y-configured fluid passageway. Ends of the two rigid tubular members 105 and 106 are telescoped into respective first ends of flexible tubular conduits 107 and 108, respectively, the respective ends of the conduits 107 and 108 being realized as respective tubular connectors 110 and 111 made of a rigid plastics material and fixedly connected to the flexible conduits 109 and 108, respectively. Opposite ends of the flexible conduits 107 and 108 are provided with respective rigid tubular connectors 112 and 113 respectively, made of a rigid plastics material. The tubular connector 112 is telescoped over one end of a tubular T-connector 114 which has an enlarged end portion 115 which is telescoped over a rigid tubular conduit 116 which is an integral part of a filter housing 117. The filter housing 117 is formed of truncated cone portions 117a and 117b which are connected together by a ridge member 117c having a circumferencially extending inwardly facing groove 117d (FIG. 9) therein. A suitable filter 118 (FIG. 9) is positioned and held firmly in the circumferencially extending groove 117d. The filter 118 with its associated housing 117 suitable for capturing particles having sizes above one micron in diameter may be realized by using a commercially available radio aerpsol filter sold under catalog No. MQ353 and available from the Marquest Medical Products, Inc., whose address is 112 Inverness Circle East, Engelwood, Colo. 80112.

Figure 9:
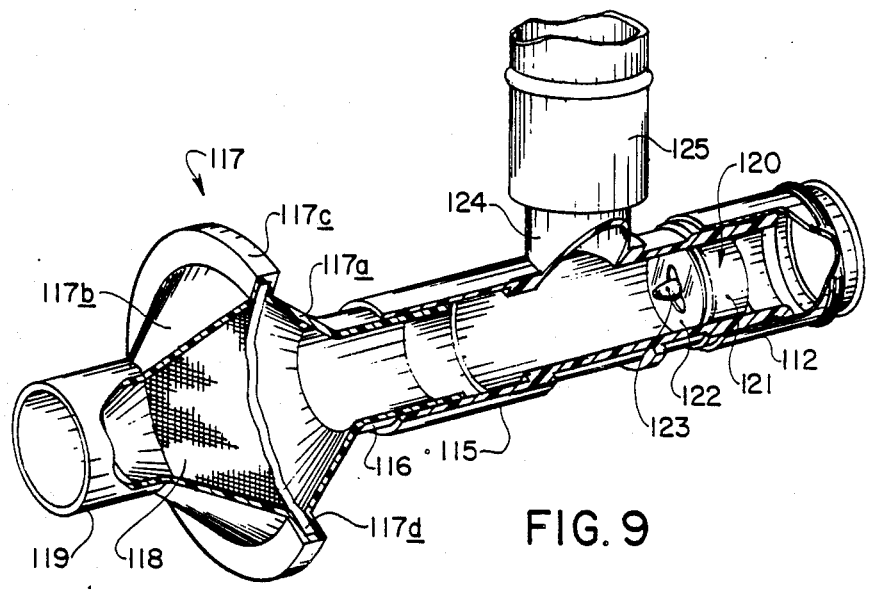
FIG. 9 is a pictorial view, partially broken away, of a portion of the device of FIG. 7, the placement of a one-way valve and filter being visible.

The tubular conduit 116, particularly visible in FIG. 9, is provided with a one-way valve structure 120. The valve structure 120 includes a cylindrical holder 121 which is fixedly connected or force fitted into the inner diameter of that tubular arm of the T-connector 114 over which the tubular connector 112 extends. A flexible diaphram 122 is carried on the downstream end of the holder 121 and is held in place by a central boss 123 which is integral with the cylindrical holder 121, a number of ribs (not visible) being provided. The flexible diaphram 122 is arranged so that when a subject exhales, the exhaled mist and radioactive particles pass from the mouthpiece 103 through the flexible conduit 107, through the tubular valve diaphram holder 121, causing the diaphram 122 to flex to the left, when viewed as illustrated in FIG. 9, allowing the exhalent to pass on and into the filter housing 117, particles of two microns and (preferably having sizes one micron and smaller) being captured by the filter 118, while air, carbon dioxide and unused oxygen passes outwardly from the device via an integral tubular extension 119 of the filter housing 117.

An opening is provided in the tubular T-connector 114 and defined by an integral tubular extension 124 which is telescoped into a rigid tubular connector which is fixedly connected to an end 125 of a flexible conduit 126; the other end of the flexible conduit 126 is provided with a rigid tubular connector 127 which is telescoped over an end 128 of a four-way passage connector 130. The four-way passage connector 130 includes a rigid tubular conduit 131 which is telescoped over one end of a further tubular conduit 132. The tubular conduit 132 is provided with a self-sealing, rubber closure member 133 through which a hypodermic needle may be passed so as to supply liquid constituting or containing radioactive material into the nebulizer 101, without removing the nebulizer 101 from the radiation-shielding container. The second rigid tubular conduit of the four-way passage connector 130 is telescoped into the rigid tubular connector 113 of the flexible conduit 108.

As shown in FIG. 10 a hypodermic syringe 134 is illustrated in position with its associated needle penetrating the self-sealing closure member 133, a hollow radiation-shielding cover 135 being shown exploded therefrom. In FIG. 11 the hollow radiation-shielding cover 135 is shown in position over the tubular extension 132 (FIG. 7) and its associated self-sealing closure member 133. This particular radiation-shielding cover 135 would be placed over the tubular extension 132 after the radioactive liquid material has been introduced into the nebulizer 101.

Figure 8:
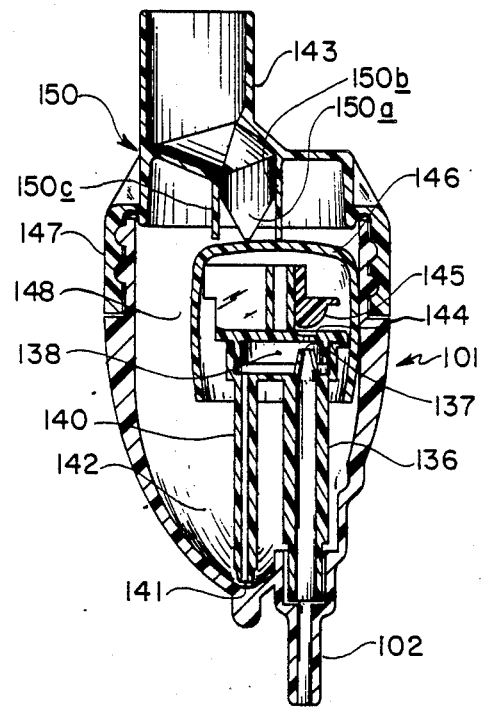
FIG. 8 is a cross-sectional view of a preferred nebulizer which may form a portion of the device of FIG. 7, the section being a longitudinal section taken along the center axis of the nebulizer.

The details of the preferred nebulizer 101 is illustrated in FIG. 8, a cross-section having been taken axially through the nebulizer 101. The nebulizer 101 includes the stem-like, tubular conduit 102 which is to be positioned into the upstanding portion 80 of the tubular member 78 (FIG. 5). The tubular conduit 102 is fluid communication with a vertically extending tubular member 136 which has a narrowing conical end portion terminating in an opening 137, air and/or oxygen under positive pressure is to pass through the tubular member 136 and out the small opening 137. The opening 137 exhausts into a chamber 138 which is in fluid communication with a downwardly extending tubular member 140 having an opening in its lower end 141 so as to be beneath the level of liquid which may contain radioactive material which is to be placed in the bottom portion 142 of the interior of the nebulizer 101. The liquid which is to be placed in the bottom portion of the nebulizer 101 is injected, as indicated above, by using the hypodermic 134 the needle of which is inserted through the self-sealing closure member 133, as shown in FIG. 10, so that the liquid will pass through and out from the arm of the four-way connector 130 (FIG. 7) into the upwardly extending tubular member 143 and thence downwardly into the nebulizer 101 collecting in the bottom portion 142 thereof. In close vicinity to the opening 137 and in the top portion of the chamber 138 is an aperture 144 having a relatively larger diameter portion at its uppermore end. The aperture 144 is positioned in close vicinity and immediately beneath a protrusion 145 which has a generally smooth arcuate outer surface. Positioned over the above-discussed structure and above the protrusion 145 is a baffle 146. The baffle 146 is force-fit over the structure defined by the tubular members 136 and 140, the chamber 138 and the protrusion 145. The baffle 146 has a smooth, arcuate inner surface on which droplets of liquid formed from aerosol mist particles having greater than one micron diameter are collected, these particles running down the inner side walls of the baffle 146 so as to again collect in the bottom portion 142 of the nebulizer 101. The nebulizer 101 is constituted by two major portions, the upper portion 147 being threadedly connected to the bottom portion, the upper portion defining internally a fluid passageway from the interior chamber 148 of the bottom portion of the nebulizer 101 and defining a passageway from the aerosol containing chamber 148 and the upstanding tubular, rigid conduit 143. A throttle 150 is provided in the passageway between the interior chamber 148 and the tubular conduit 143, the passageway constituting a pre-determined restriction, so far as cross-section is concerned, to allow selection of the desired and/or prescribed amount of radiological material which a subject is to inhale during a given test. The throttle 150 is constituted by a plurality of downwardly extending triangularly shaped extensions **150*a*–150*c*, these extensions being bendable (when subjected to a heat treatment) so as to provide selectively a particular opening area from the chamber 148 into the rigid tubular conduit 143. As illustrated, the triangular extensions 150*a*–150*c* are shown unbent in positions providing a maximum opening area. Were one to desire a more restrictive opening, so as to subject a subject to a lesser dose of radioactive material, the end portions of the triangular extensions 150*a*–150*c* would simply be bent inwardly so as to make the opening smaller in area. As a practical matter a number of threaded upper members 147**, possibly color coded, could be provided so that a user could select which ever throttle opening area feature was desired in a given case.

The method of the present invention, in all of its aspects, is set out above in the summary section. It can be carried out using the embodiments of the apparatus and the embodiments of the device described in detail above.

FIG. 12 pictorially illustrates details of a preferred embodiment of a device constructed in accordance with the present invention, like reference numerals referring to like portions and components as corresponding numerals used in FIGS. 7–9. For the sake of succinctness, a detailed rediscription of these common portions and components is not needed.

As illustrated in FIG. 12, the self-sealing closure member 133 removably positioned on the tubular conduit 132 is provided centrally on its outwardly facing surface with a circular index line 155, which defines within the circle a target into which the physician or technician is to insert the needle of a syringe (FIG. 10). The closure member 133 has an inward portion 156 of reduced external diameter which corresponds to the inner diameter of the conduit 132. An end of a tube 157 is positioned within a central bore extending partially through the closure member 133, the end of the tube being positioned beneath and spaced from the target defined by the circular line 155. The tube 157 extends along the interior of the tubular conduit 132, is bent downwardly at about the center of the four-way passage connector 130 so that it is substantially perpendicular. The downwardly facing open end of the tube 157 is positioned above the nebulizer 101, so that the liquid containing radioactive material can be effectively delivered to the interior of the nebulizer. The portion of the tube 157 extending from the closure member 133 to the bend serves as a guide for the needle of the syringe, allowing one to avoid delivering the material in a fashion which may result in the material flowing and spreading along the interior surface of the tubular conduit 132.

The device of FIG. 12 includes the one-way valve structure 120, as shown in detail in FIG. 9. The device includes additionally a one-way valve structure 151 composed of a cylindrical holder 152 fixedly connected or force fitted into the inner diameter of the tubular connector 127 (FIG. 7, broken away in FIG. 12). A flexible diaphram 153 is carried by a central boss 154 which is carried on ribs extending inwardly from the holder 152. The one-way valve structure 151 allows fluid communication from the conduit 107 and the filter 117 to the conduit 108, and prevents fluid communication from the conduit 108 and the nebulizer 101 to the conduit 107 and to the filter 117. The one-way valve structure 151 reduces back pressure to the subject and allows the device to operate more efficiently, virtually no radio-active material being directly delivered from the nebulizer to the filter.

From the foregoing it will be seen that applicants' pulmonary inhalation apparatus and device provides for a disposable aerosol inhalation device which generates properly sized radioactive particles having provisions for proper valving, proper nondisposable shielding, and ease of operation. Further, the apparatus and device has been described with reference to particular embodiments which have been set out, not by way of limitation, but by way of illustration. The embodiments of the apparatus and the device can be used in conjunction with ventilators and respirators, appropriate controlled valves being added. It is to be appreciated that many other embodiments and variants are possible within the spirit and scope of the invention, its scope being defined by the appended claims.

What is claimed is:

1. An aerosol inhalation apparatus for supplying an aerosol mist containing radioactive tagged particles to a subject, comprising a reusable radiation-shielding container having lid means, whereby the contents of the container are readily accessible, and a disposable radioactive aerosol inhalation device, the device including first and second conduit means in said container and passing therethrough, means for communicating with an air passageway of a subject connected to the first and second conduit means externally of said container, valve means for controlling exhalation from said second conduit means, a nebulizer within said container and connected to said first conduit means, means positioned at least in part within the container and in fluid communication with said nebulizer for allowing introduction of radioactive solution from outside said container into said nebulizer, means associated with said nebulizer for generating an aerosolized mist carrying radioactive tagged particles, means for introducing a mixture of air or oxygen and the mist into said first conduit means, third conduit means within said container interconnecting said first conduit means and said second conduit means, and entrapping filter means in said container and connected to said second conduit means for removing the aerosol exhaled, whereby the container may be reused and the device may be discarded after each use.

2. The aerosol inhalation apparatus according to claim 1, wherein said valve means is positioned within a portion of said second conduit means, said portion being within said container, and wherein said third conduit means is connected to said second conduit means downstream from said valve means.

3. The aerosol inhalation apparatus according to claim 2, wherein said valve means is a one-way valve means.

4. The aerosol inhalation apparatus according to claim 1, wherein said valve means comprises first one-way valve means positioned within a portion of said second conduit means and a second one-way valve means positioned with a portion of said third conduit means.

5. The aerosol inhalation apparatus according to claim 1, wherein said valve means is a one-way valve means.

6. The aerosol inhalation apparatus according to claim 1, wherein said means carried by said container for allowing introduction of a radioactive solution into said nebulizer comprises means in fluid communication with said nebulizer and with said first conduit means for permitting entry of atmospheric air into said nebulizer and into said first conduit means.

7. The aerosol inhalation apparatus according to claim 1, including means positioned within said container for removably fixing said device to said container, and means accessible from outside said container for unfixing said device from said container.

8. The aerosol inhalation apparatus according to claim 7, wherein said means accessible from outside said container for unfixing said device from said container includes a pivoted member, said pivoted member being pivoted about an axis intermediate its end portions, one of its end portions being positioned beneath said nebulizer, and an operator accessible to a user being coupled to its second end portion.

9. The aerosol inhalation apparatus according to claim 1, wherein said means for allowing introduction of a radioactive solution is an angulated port allowing a needle to extend into said container at an angle with respect to vertical to minimize exposure to radiation.

10. The aerosol inhalation apparatus according to claim 1, wherein said nebulizer includes a settling baffle to generate properly sized aerosol particles of less than substantially one micron.

11. The aerosol inhalation apparatus according to claim 10, wherein said nebulizer includes a diffuser and gas orifice, said settling baffle being positioned above said diffuser and said gas orifice for permitting aerosol particles larger than substantially one micron to remain in said nebulizer.

12. An aerosol inhalation apparatus for supplying an aerosol mist containing radioactive tagged particles to a subject, comprising a reusable generally cylindrical walled container having a closed bottom and an open top, radiation-shielding means within said wall and bottom of the container, the container having first, second and third openings formed therein, respectively, said openings being at the top portion of said container and being circumferentially spaced from each other, radiation-shielding lid means covering said container top portion, and a disposable pulmonary inhalation device including nebulizing means in said container, entrapping filter means within said container, means received in said first of said openings and including a conduit connected to said nebulizer means for introducing a radioactive liquid into said nebulizer means, means associated with said nebulizer means for generating an aerosolized mist having a plurality of radioactive tagged particles, inhalation conduit means received in said second of said openings and connected to said nebulizer means, and exhalation conduit means received in said third of said openings and connected to said filter means, and further conduit means within said container interconnecting said inhalation conduit means and said exhalation conduit means, whereby the container may be reused and the device may be discarded after each use.

13. An aerosol inhalation apparatus according to claim 12, wherein said first, second and third openings are constituted by respective slots extending downwardly from a top edge of said container.

14. The aerosol inhalation apparatus according to claim 12, including means positioned within said container for removably fixing said device to said container, and means accessible from outside said container for unfixing said device from said container.

15. The aerosol inhalation apparatus according to claim 14, wherein said means accessible from outside said container for unfixing said device from said container includes a pivoted member, said pivoted member being pivoted about an axis intermediate its end portions, one of its end portions being positioned beneath said nebulizer, and an operator accessible to a user being coupled to its second end portion.

16. An aerosol inhalation apparatus for supplying an aerosol mist containing radioactive tagged particles and air and/or oxygen to a subject, comprising a reusable radiation-shielding container having lid means, whereby the contents of the container are readily accessible, and a disposable radioactive aerosol inhalation device, the device including first and second conduit means in said container and passing therethrough, means for communicating with an air passageway of a subject connected to the first and second conduit means externally of said container, valve means for controlling exhalation from said second conduit means, a nebulizer within said container and connected to said first conduit means, means positioned at least in part within the container and in fluid communication with said nebulizer for allowing introduction of radioactive solution from outside said container into said nebulizer, means in fluid communication with a source of air and/or oxygen, and with said nebulizer associated with said nebulizer for generating an aerosolized mist carrying airborne radioactive tagged particles, means for introducing a mixture of air and/or oxygen, and the mist into said first conduit means, third conduit means within said container interconnecting said first conduit means and said second conduit means, and entrapping filter means in said container and connected to said second conduit means for removing the aerosol exhaled, whereby the container may be reused and the device may be discarded after each use.

17. The aerosol inhalation apparatus according to claim 16, including further valve means positioned within said third conduit means for allowing fluid communication from said second conduit means to said first conduit means and for preventing fluid communication from said first conduit means and said nebulizer to said second conduit means.

18. The aerosol inhalation apparatus according to claim 16, wherein said means carried by said container for allowing introduction of a radioactive solution into said nebulizer comprises means in fluid communication with said nebulizer and with said first conduit means for permitting entry of atmospheric air or other ambient into said nebulizer and into said first conduit means.

19. The aerosol inhalation apparatus according to claim 18, wherein said nebulizer a diffuser, a settling baffle and gas orifice, said settling baffle being positioned above said diffuser and said gas orifice for permitting aersol particles larger than substantially one micron to remain in said nebulizer.

20. The aerosol inhalation apparatus according to claim 16, wherein said means for allowing introduction of a radioactive solution is an angulated port allowing a needle to extend into said container at an angle with respect to vertical to minimize exposure to radiation.

21. The aerosol inhalation apparatus according to claim 16, including a settling baffle in said nebulizer to generate properly sized aerosol particles of less than substantially one micron.

22. The aerosol inhalation apparatus according to claim 16, including means positioned within said container for removably fixing said device to said container, and means accessible from outside said container for unfixing said device from said container.

23. The aerosol inhalation apparatus according to claim 22, wherein said means accessible from outside said container for unfixing said device from said container includes a pivoted member, said pivoted member being pivoted about an axis intermediate its end portions, one of its end portions being positioned beneath said nebulizer, and an operator accessible to a user being coupled to its second end portion.

24. An aerosol inhalation apparatus for supplying an aerosol mist containing radioactive charged particles and air and/or oxygen to a subject, comprising a reusable generally cylindrical walled container having a closed bottom and an open top, lead radiation-shielding means within said wall and said bottom of the container, the container having first, second and third openings formed therein, respectively, said openings being at the top portion of said container and being circumferentially spaced from each other, lead radiation-shielding lid means covering said container top portion, a disposable pulmonary inhalation device including nebulizing means in said container, entrapping filter means within said container, means received in said first of said openings and including a conduit connected to said nebulizer means for introducing a radioactive liquid into said nebulizer means, means associated with nebulizer means for generating an aerosolized mist having a plurality of radioactive tagged particles, inhalation conduit means received in said second of said openings and connected to a source of air and/or oxygen and to said nebulizer means for receiving a mixture of air and/or oxygen and the mist, exhalation conduit means received in said third and of said openings and connected to said filter means, and further conduit means interconnecting said inhalation conduit means and said exhalation conduit means, whereby the container may be reused and the device may be discarded after each use.

25. An aerosol inhalation apparatus according to claim 24, wherein said first, second and third openings are constituted by respective slots extending downwardly from a top edge of said container.

26. The aerosol inhalation apparatus according to claim 24, including means positioned within said container for removably fixing said device to said container, and means accessible from outside said container for unfixing said device from said container.

27. The aerosol inhalation apparatus according to claim 26, wherein said means accessible from outside said container for unfixing said device from said container includes a pivoted member, said pivoted member being pivoted about an axis intermediate its end portions, one of its end portions being positioned beneath said nebulizer, and an operator accessible to a user being coupled to its second end portion.

28. An aerosol inhalation device for supplying an aerosol mist to a subject, the device comprising first and second conduit means, means for communicating with an air passageway of a subject connected to the first and second conduit means, valve means for controlling exhalation from said second conduit means, a nebulizer coupled to said first conduit means, means in fluid communication with said nebulizer for allowing introduction of liquid into said nebulizer, means associated with said nebulizer for generating an aerosolized mist carrying airborne particles, third conduit means interconnecting said first conduit means and said second conduit means, and means for introducing a mixture of air and-/or oxygen, and the mist into said first conduit means.

29. The aerosol inhalation device according to claim 28, wherein said valve means is positioned within said second conduit means, and wherein said third conduit means is in fluid communication with said second conduit means downstream from said valve means.

30. The aerosol inhalation device according to claim 29, wherein said valve means is a one-way valve means.

31. The aerosol inhalation device according to claim 28, wherein said valve means comprises first one-way valve means positioned within a portion of said second conduit means and a second one-way valve means positioned within said third conduit means.

32. The aerosol inhalation device according to claim 28, wherein said means for allowing introduction of a liquid into said nebulizer comprises means in fluid communication with said nebulizer and with said first conduit means for permitting entry of atmospheric air into said nebulizer and into said first conduit means.

33. The aerosol inhalation device according to claim 32, including a settling baffle within said nebulizer, said baffle having an inner surface defined by an arcuate dome.

34. The aerosol inhalation device according to claim 32, including throttle means disposed in fluid communication path between said nebulizer and said first conduit means.

35. The inhalation device according to claim 34, wherein said throttle means is changeable or adjustable.

36. The aerosol inhalation device according to claim 28, including a settling baffle in said nebulizer to generate aerosol particles of less than substantially one micron.

37. The aerosol inhalation device according to claim 36, wherein said nebulizer includes a diffuser and gas orifice, said settling baffle being positioned above said diffuser and said gas orifice for permitting aerosol particles larger than substantially one micron to remain in said nebulizer.

38. In an aerosol inhalation apparatus for supplying an aerosol mist containing radioactive tagged particles to a subject and including a disposable aerosol inhalation device and radiation-shielding container means, at least a portion of the device being removably fixed within said container means, an improvement comprising means at least partially positioned within said container and accessible from outside said container for unfixing, the device from said container.

39. An improved aerosol inhalation apparatus according to claim 38, wherein said means positioned within said container and accessible from outside said container includes a pivoted member pivoted about an axis intermediate its end portions, one of said end positions being positioned beneath a portion of said device to unfix said device from said container, an operator accessible to a user being coupled to its other end portion.

40. An aerosol inhalation device for supplying an aerosol mist to a subject, the device comprising first and second conduit means, means for communicating with an air passageway of a subject connected the first and second conduit means, valve means for controlling exhalation from said second conduit means, throttle means coupled to said first conduit means, a nebulizer coupled to said first conduit means via said throttle means, means in fluid communication with said nebulizer for allowing introduction of liquid into said nebulizer, means associated with said nebulizer for generating an aerosolized mist, third conduit means interconnecting said first conduit means and said second conduit means, and means for introducing a mixture of air and-/or oxygen, and the mist into said first conduit means.

41. The aerosol inhalation device according to claim 40, wherein said valve means is positioned within said second conduit means, and wherein said third conduit means is in fluid communication with said second conduit means downstream from said valve means.

42. The aerosol inhalation device according to claim 41, wherein said valve means is a one-way valve means.

43. The aerosol inhalation device according to claim 40, wherein said valve means comprises first one-way valve means positioned within a portion of said second conduit means and a second one-way valve means positioned within said third conduit means.

44. An aerosol inhalation device for supplying an aerosol mist to a subject, the device comprising first and second conduit means, means for communicating with an air passageway of a subject connected to the first and second conduit means, valve means for controlling exhalation from said second conduit means, throttle means coupled to said first conduit means, a nebulizer coupled to said first conduit means via said throttle means, means in fluid communication with said nebulizer for allowing introduction of liquid into said nebulizer, means associated with said nebulizer for generating an aerosolized mist, and means for introducing a mixture of air and/or oxygen, and the mist into said first conduit means.

45. The aerosol inhalation device according to claim 44, wherein said valve means is positioned within said second conduit means.

46. The aerosol inhalation device according to claim 45, wherein said valve means is a one-way valve means.

47. The aerosol inhalation device according to claim 44, including third conduit means interconnecting said first and second conduit means, wherein said valve means comprises first one-way valve means positioned within a portion of said second conduit means and a second one-way valve means positioned within said third conduit means.

* * * * *